United States Patent
Smith (10) Patent No.: US 9,615,776 B2
(45) Date of Patent: Apr. 11, 2017

(54) SIGNAL PROCESSING METHOD AND APPARATUS

(75) Inventor: Stephen Smith, York (GB)

(73) Assignee: Clearsky Medical Diagnostics Limited (GB)

( * ) Notice: Subject to any disclaimer, the term of this patent is extended or adjusted under 35 U.S.C. 154(b) by 488 days.

(21) Appl. No.: 13/980,320

(22) PCT Filed: Jan. 18, 2012

(86) PCT No.: PCT/GB2012/050093
§ 371 (c)(1),
(2), (4) Date: Oct. 7, 2013

(87) PCT Pub. No.: WO2012/098388
PCT Pub. Date: Jul. 26, 2012

(65) Prior Publication Data
US 2014/0155784 A1    Jun. 5, 2014

(30) Foreign Application Priority Data
Jan. 18, 2011    (GB) .................................. 1100794.5

(51) Int. Cl.
*A61B 5/11* (2006.01)
*G06K 9/00* (2006.01)
*G06K 9/62* (2006.01)

(52) U.S. Cl.
CPC .......... *A61B 5/1101* (2013.01); *A61B 5/1125* (2013.01); *G06K 9/00536* (2013.01); *G06K 9/6229* (2013.01)

(58) Field of Classification Search
CPC ............................ A61B 5/1101; A61B 5/1125
See application file for complete search history.

(56) References Cited

PUBLICATIONS

International Search Report for corresponding patent application No. PCT/GB2012/050093 dated Apr. 16, 2012.
Kim et al.; "Quantification of bradykinesia during clinical finger taps using a gyrosensor in patients with Parkinsona's disease", Medical & Biological Engineering & Computing, vol. 49, No. 3, Oct. 30, 2010.
Smith et al.; "Diagnosis of Parkinson's disease using evolutionary algorithms"; Genetic Programming and Evolvable Machines, Kluwer Academic Publishers, vol. 8, No. 4, Oct. 4, 2007.
Allen et al.; "On the Use of Low-Cost Computer Peripherals for the Assessment of Motor Dysfunction in Parkinson's Disease—Quantification of Bradykinesia Using Target Tracking Tasks"; IEEE Transactions on Neural Systems and Rehabilitation Engineering, IEEE Service Center, vol. 15, No. 2, Jun. 1, 2007.
Smith et al.; "Implicit Context Representation Cartesian Genetic Programming for the assessment of visuo-spatial ability"; Evolutionary Computation, IEEE Congress, pp. 1072-1078, May 18, 2009.

(Continued)

*Primary Examiner* — Adam J Eiseman
*Assistant Examiner* — Yasmeen S Warsi
(74) *Attorney, Agent, or Firm* — Renner, Otto, Boisselle & Sklar, LLP (57) ABSTRACT

The invention provides signal processing algorithms and apparatus for detecting bradykinesia, tremor, or other symptoms of neurological dysfunction in subjects, using three-dimensional sensors to tract finger and hand position. The invention provides Cartesian Genetic Programming networks and particular function blocks for such networks to enable identification of subjects exhibiting such symptoms.

14 Claims, 4 Drawing Sheets

(56) References Cited

PUBLICATIONS

Smith et al.; "An immune network inspired evolutionary algorithm for the diagnosis of Parkinson's disease", Biosystems, North-Holland, vol. 94, No. 1-2, Oct. 1, 2008.
Smith et al.; "The Application of Evolutionary Algorithms towards the Diagnosis of Parkinson's Disease"; Genetic and Evolutionary Computation Conference, Jul. 1, 2006.

SIGNAL PROCESSING METHOD AND APPARATUS

This application is a national phase of International Application No. PCT/GB2012/050093 filed Jan. 18, 2012 and published in the English language.

FIELD OF THE INVENTION

The invention relates to methods of generating signal processing algorithms for processing signals representing the time-varying spatial position of a subject's fingers or the relative position of a subject's finger and thumb for identifying subjects exhibiting bradykinesia and/or tremor, or symptoms of other neurological dysfunctions. The invention also relates to apparatus and methods using algorithms so developed.

BACKGROUND AND PRIOR ART KNOWN TO THE APPLICANT

Parkinson's disease (PD) is a chronic, progressive, neurodegenerative disorder, which occurs as a result of the loss of dopaminergic neurons in the brain, but whose cause is unknown. PD was first written about by English physician, James Parkinson in 1817. He described the illness in an essay titled 'The Shaking Palsy', as an "involuntary tremulous motion, with lessened muscular power, in parts not in action even when supported, with a propensity to bend the trunk forward and to pass from a walking to a running pace". This statement described many of the features that are associated with PD today.

The onset of PD is very gradual and many patients cannot remember when their symptoms began. The early symptoms of PD are often vague and non-specific, and amongst many other symptoms often include tiredness, fatigue, weariness, muscle aches, and cramps. There are three cardinal motor features of PD; these are tremor, rigidity and bradykinesia.

In literature, bradykinesia, akinesia and hypokinesia are commonly confused. Bradykinesia is defined as a slowness of ongoing movement, whereas akinesia is failure to initiate a willed movement, and hypokinesia is the reduction of movement. It is not known if these features are related, although one study evaluated the relation between bradykinesia and hypokinesia and concluded a lack of relation between the two features. This means that in literature 'bradykinesia' is often used to encompass many different aspects of poverty of movement; including prolonged reaction time to initiate a movement, prolonged time to discontinue a false movement, prolonged time to change a motor pattern, rapid fatigue on long tasks and slow execution of movement (see e.g van Hilten, J., et al., "*Bradykinesia and hypokinesia in Parkinson's disease: What's in a Name?*", Journal of Neural Transmission, Vol. 105, 1998, pp. 229-237). Several proposals have been offered as explanations for why PD subjects move more slowly than normal subjects, although a single mechanism has not been achieved. These proposals include suggestions that bradykinesia results from a lower production of force, that PD subjects adopt a behavioural strategy of moving slowly in order to maintain their accuracy, and that bradykinesia may result from a basic defect in ability to internally organise motor output (Majsak, M., et al., "*The reaching movements of patients with Parkinson's disease under self-determined maximal speed and visually cued conditions*", Brain, Vol. 121, 1998, pp. 755-766).

A Berrardelli, et al. ("*Pathophysiology of bradykinesia in Parkinson's disease*", Brain, Vol. 124, 2001, pp. 2131-2146) have considered five factors that contribute to bradykinesia. These are:

i. muscle weakness, which is likely to contribute to slowness of movement in some muscle groups;
ii. rigidity, which may lead to slower reflexes;
iii. tremor, which may be a factor in prolonging reaction times and the persistence of action tremor may lead to muscle weakness;
iv. movement variability, whereby PD subject's movements are less accurate than normal subjects, particularly when they have to move quickly; and
v. slowness of thought (bradyphrenia), which could interfere with movement planning and increase movement time.

Bradykinesia is commonly observed in patients as facial immobility (hypomimia), infrequent blinking, paucity of normal gesture and lack of expression, as well as sudden stopping of ongoing motion, known as 'freezing'. Bradykinesia is thought to be present in 77-98% of cases of PD; however it also occurs in many other related disorders (including progressive supranuclear palsy, multiple system atrophy, Alzheimer's disease and depression) and is also common in old age ("*Pathophysiology of bradykinesia in Parkinson's disease*", Brain, Vol. 124, 2001, pp. 2131-2146).

There are many other features that are related to PD, apart from the cardinal symptoms described above. Other features include: reduced arm swing on walking, stooped posture with shuffling gait, falls; micrographia (small and illegible handwriting), due to the clumsiness of hand movements and difficulty with fine motor tasks, Parkinsonian dysarthria (speech disorders). These are estimated to be present in more than 75% of PD patients and may consist of reduced loudness, monotone, imprecise articulation, and/or disordered rate, Dysphagia (difficulty in swallowing) which may lead to drooling of saliva and poor nutritional status, bradyphrenia (slowness of thought), depression which is estimated to be present in 40-50% of patients, cognitive problems and dementia which are estimated to be present in 48-80% of patients, olfactory dysfunction (lack of sense of smell) which is thought to affect 70% of patients and sleep disorders.

The term 'Parkinsonism' refers to any condition which shows the common motor symptoms of PD (tremor, rigidity and bradykinesia), therefore some patients with Parkinsonism do not have idiopathic Parkinson's disease (referred to in this study simply as Parkinson's Disease). PD is the most common cause of these symptoms, however a study of patients with Parkinsonism found that 65% had PD, 18% had drug-induced Parkinsonism, 7% had vascular Parkinsonism (caused by blockages in the small blood vessels feeding the brain) and 10% had atypical Parkinsonism. The most common atypical Parkinsonism syndromes are multiple system atrophy (MSA) and progressive supranuclear palsy (PSP), but also include diffuse Lewy body disease, corticobasal degeneration and overexposure to certain substances (e.g. manganese and MPTP).

Thus, bradykinesia is an important element in the diagnosis of a disease or responses to drugs or toxins. Although having a central role in the diagnostic armoury, the identification of the presence of bradykinesia is not itself a diagnosis of any particular clinical condition.

The tapping test is used routinely for the quantification of drug effects on motor slowness in PD and is described below.

Many different types of equipment have been used to measure the tap rate of PD patients, including: electronic touchpads with touch plates (Muir, S., et al., "Measurement and Analysis of Single and Multiple Finger Tapping in Normal and Parkinsonian Subjects", Parkinsonism & Related Disorders, Vol. 1, No. 2, 1995, pp. 89-96); a computer keyboard (Giovanni, G. et al., "Bradykinesia akinesia inco-ordination test (BRAIN TEST): an objective computerised assessment of upper limb motor function", J Neurol Neurosurg Psychiatry, Vol. 67, 1999, pp. 624-629), computer-interfaced musical keyboards (Tavares, A., et al., "Quantative Measurements of Alternating Finger Tapping in Parkinson's Disease Correlate With UPDRS Motor Disability and Reveal the Improvement in Fine Motor Control From Medication and Deep Brain Stimulation", Movement Disorders, Vol. 20, No. 10, pp. 1286-1298, 2005), buttons (interfacing a microcomputer) and accelerometers (Dunnewold, R., Jacobi, C. & van Hilten, J., "Quantitative assessment of bradykinesia in patients with Parkinson's disease", Journal of Neuroscience Methods, Vol. 74, 1997, pp. 107-112).

All of the studies described above found that PD patients had a significantly lower tap rate than normal control subjects. Many studies have found that the tap rate correlates well with ratings given from the motor sections of the UPDRS scale.

R. Dunnewold, et al. measured the movement time of subjects along with the tapping score. The movement time used in this study was calculated as the time for a subject to react to visual stimuli on a video display. It was found that a correlation above 0.75 was found between the tapping rate and the movement time of the subjects, however low correlations were found between the score from the motor section of the UPDRS scale and the tap rate and movement time. Many other studies have also considered reaction time (time from the 'go' signal until the onset of movement) and movement time (time between movement onset and reaching target) of subjects in response to various stimuli. Movement time is the physiologic correlate of bradykinesia, and reaction time is the correlate of akinesia. These studies discovered that PD patients exhibit a significantly prolonged reaction time compared to controls.

R. Watts, et al. ("Electrophysiologic analysis of early Parkinson's disease", Neurology, Vol. 41, Supplement 2, 1991) used a simple touchpad with a 'start' location and two 'target' locations to measure reaction time. Two tasks were used; the first where the target location was specified before the 'go' signal was given, and a second where the target location was shown on the 'go' signal. It was found that reaction time was prolonged in PD patients compared to controls where the target location was predefined, but not where the subjects had to choose the target on the 'go' signal. Movement time was found to be prolonged in both tasks for PD subjects compared to controls.

M. Zappia, et al. (Zappia, M., et al., "*Usefulness of movement time in the assessment of Parkinson's disease*", J Neurol, Vol. 241, 1994, pp. 543-550) compared movement time and reaction time, before and after Levodopa administration. It was found that off treatment, movement time and reaction time of the most affected side were significantly related to the severity of PD. After Levodopa administration the movement time improvement related to the severity of PD, whereas reaction time did not.

M. Hallett and S. Khoshbin ("*A Physiological Mechanism of Bradykinesia*", Brain, Vol. 103, 1980, pp. 301-314) carried out a study in 1980 into rapid elbow movements of the dominant arm in PD patients and controls. The subjects were seated in a chair with their arm strapped to a splint with a potentiometer incorporated into the hinge, which was able to convert the rotation of the elbow into a variable voltage. The subjects made fast, accurate elbow flexion movements, beginning at 120°, moving to 80°, 100° and 110°. It was found that normal subjects made all of these movements in the same amount of time with a single 'triphasic' pattern of successive bursts of the bicep, tricep and bicep muscles. Most PD patients exhibited alternate bursts longer than the three bursts of activity seen in the controls (up to twelve bursts), which tended to occur more for the longer movements. This is thought to represent a physiological mechanism of bradykinesia.

K. Maitra and A. Dasgupta ("*Usefulness of movement time in the assessment of Parkinson's disease*", J Neurol, Vol. 241, 1994, pp. 543-550) performed a study using fast reach-to-grasp movements without any visual stimuli in PD patients. Movement of the subject's upper arm (measure of reach) and movement of the index finger (measure of grasp) were recorded using magnetic trackers. The experiment was conducted in a dimly lit room, where subjects stood with their upper arm by the side of their body and on the command of 'go', performed a fast reaching and grasping movement without any physical object to grasp. It was found that the controls performed each movement rapidly with a smooth single peak velocity with near symmetrical acceleration and deceleration phases. The angular movements were found to have minimal variability under repetitive trials. The PD patients however, moved much slower with less amplitude and greater variability over repeated trials. The total movement in PD patients seemed to be sequential, rather than continuous as seen in the control patients. It was concluded that bradykinesia in participants with PD resulted from a defect in switching from one motor programme to another.

The tapping test is used routinely for the quantification of drug effects on motor slowness in PD, and many different types of equipment have been used to measure the tap rate of PD patients in previous studies. A number of studies have also considered reaction time and movement time of subjects in response to a stimulus. Bradykinesia is measured in the UPDRS scale by asking patients to perform finger taps, hand movements and rapid alternating movements of hands, in both the left and right hands. The tasks used to measure bradykinesia in the UPDRS scale are shown below:

The tapping test is commonly performed by subjects tapping their thumb with their index finger as many times as possible in 30 seconds for each hand.

The tasks chosen to observing resting tremor and bradykinesia in this study were both hand-based, so collection of the most useful data was obtained by attaching the sensors to the hands of the participating subjects. As the tapping test involved the thumb and index finger of the subjects, sensors for the bradykinesia task were attached on the thumb and index finger. During the tapping test most movement of the fingers occurs at the end of the digits, therefore it was decided that one of the sensors would be placed on the nail of the subject's thumb and the other sensor on the nail of the subject's index finger.

However there are no reliable techniques for the detection of bradykinesia, therefore the inventors have employed novel computing techniques for the detection of bradykinesia.

SUMMARY OF THE INVENTION

Accordingly, in a first aspect, the inventor provides a method of generating a signal processing algorithm for processing signals representing finger and thumb positions for identifying subjects exhibiting bradykinesia or tremor at a required discrimination confidence, said method comprising the steps of:

(1) providing a plurality of patient position data sets, each set representing a time series of three-dimensional position data of finger and thumb during tapping tests from each of a plurality of subjects exhibiting bradykinesia or tremor;

(2) providing a plurality of control position data sets, each set representing time series of three-dimensional position data of finger and thumb during tapping tests from each of a plurality of control subjects;

(3) processing said position data sets to produce patient acceleration data sets and control acceleration data sets representing time series of acceleration of the finger relative to the thumb for each corresponding tapping test;

(4) providing a set of function blocks for construction of a Cartesian Genetic Programming (CGP) network;

(5) providing a fitness function giving a measure of the success of said CGP network in discriminating between said control acceleration data set and said patient acceleration data set;

(6) configuring an initial CGP network using said function blocks, said network accepting a plurality of input data comprising adjacent values in an acceleration data set and producing a single output value putatively indicative of the presence or absence of bradykinesia or tremor;

(7) evolving said initial CGP network by sequential evolutionary mutation and selection towards increased fitness until said desired discrimination confidence is achieved.

The "tapping test" is used routinely in clinical investigation for the quantification of drug effects on motor slowness in PD, and is well-known to those skilled in the art. The test is described in e.g. Boraud, T., Tison, F. & Gross, C., "Quantification of Motor Slowness in Parkinson's Disease: Correlation Between the Tapping Test and Single Joint Ballistic Movement Parameters", Parkinsonism & Related Disorders, Vol. 3, No. 1, 1997, pp. 47-50. In the tapping test, subjects have to perform as many taps as possible in a set time. In the often-used UPDRS scale (Unified Parkinson's Disease Rating Scale) the tapping test is used to evaluate bradykinesia, where patients are asked to tap their thumb with their index finger in rapid succession and the number of taps in 30 seconds is counted. Thus, for providing appropriate data sets for the generation of such a signal processing algorithm, finger and thumb positional data are preferably gathered over a time interval of approximately 30 seconds, say for at least 20 seconds, and preferably for at least 30 seconds.

Appropriate position sensors that may be used to gather the data sets will be described below. The inventors have found that a data sampling rate of at least 10 Hz is required; preferably, the sampling rate is at least 20 Hz, or even at least 30 Hz, 50 Hz or 60 Hz. These sampling rates allow sufficient data to be captured over the expected timescales of the tapping task.

Previous studies in the machine measurement of bradykinesia have been limited to two-dimensional tasks such as tracing shapes on a graphics tablet. The inventors have found that improved discrimination of the presence or absence of bradykinesia may be obtained by the use of three-dimensional sensors of finger position, thereby providing a test that is more familiar to attending clinicians, and more able to be compared with existing studies using a manual test. Whilst previous attempts have been made to "automate" the interpretation of tapping test results, these have been primarily concerned with the measurement of tap rate. The present invention removes the constraint of requiring a pre-determined feature to form the basis of the assessment, and allows the power of evolutionary algorithms to evolve a signal processing scheme without such constraints. In this way, hitherto unknown features of the movement of a subject's finger and thumb may be brought into play within the discriminatory algorithm.

Furthermore, allowing such a test to take place in three-dimensions (i.e. without constraining subject movements to a plane) allows the test to be less stressful for the patient, many of whom might have associated symptoms of stress, depression and dementia.

The skilled addressee will be able to select methods for extracting acceleration data from the positional data sets. However, particularly preferred methods will be described herein, having particular advantage in the generation of appropriate algorithms.

The skilled addressee will, given the teaching herein, be able to construct a CGP network to process the data sets. Similar networks are described in Smith, S. L. et al, Genet. Program. Evolvable. Mach. (2007) 8:433-447. Particularly suitable networks will also be described in more detail below.

Preferably, the processing of position data sets in step (3) comprises intermediate calculation of patient and control velocity data sets representing a time series of velocity data of the finger relative to the thumb for each corresponding tapping test, said velocity data sets being smoothed using a moving average filter of window size 2. Surprisingly, the inventors have found that the use of a moving average filter of window size 2 provides the optimum filtering to remove noise artefacts whilst retaining sufficient information content within the data to allow the evolved algorithm to function correctly. Window sizes of more than 3 result in algorithms having reduced fitness. The moving average filter has the form $y_n = 0.5*(x_n + x_{n-1})$ where y is the filter output for data point n and x is the input data.

In any aspect of the invention, it is preferred that the processing of position data sets in step (3) comprises intermediate calculation of patient and control velocity data sets representing a time series of velocity data of the finger relative to the thumb for each corresponding tapping test, said velocity data sets being clipped to within one standard deviation of the mean velocity.

In a second related aspect, the invention provides a method of generating a signal processing algorithm for processing signals representing finger and thumb positions for identifying subjects exhibiting bradykinesia, tremor, or symptoms of other neurological dysfunction at a required discrimination confidence, said method comprising the steps of:

(1) providing a plurality of patient position data sets, each set representing a time series of three-dimensional position data of a subject's fingers/thumb during motor function tests from each of a plurality of subjects exhibiting bradykinesia, tremor, or symptoms of other neurological dysfunction;

(2) providing a plurality of control position data sets, each set representing time series of three-dimensional position data of a subject's fingers during motor function tests from each of a plurality of control subjects;

(3) processing said position data sets to produce patient acceleration data sets and control acceleration data sets representing time series of acceleration of the fingers for each corresponding motor function test;

(4) providing a set of function blocks for construction of a Cartesian Genetic Programming (CGP) network;

(5) providing a fitness function giving a measure of the success of said CGP network in discriminating between said control acceleration data set and said patient acceleration data set;

(6) configuring an initial CGP network using said function blocks, said network accepting a plurality of input data comprising adjacent values in an acceleration data set and producing a single output value putatively indicative of the presence or absence of bradykinesia, tremor, or other neurological dysfunction;

(7) evolving said initial CGP network by sequential evolutionary mutation and selection towards increased fitness until said desired discrimination confidence is achieved.

In a preferred embodiment of this second aspect, the motor function test comprises a constructional task such as the tracing of a geometric figure. Particularly suitable geometric figures include polygonal spirals, interlinked pentagons and wire cube.

In a further preferred embodiment of this second aspect, the motor function test comprises a prehension test such as a "reach and grasp" task.

Also in any aspect of the invention, it is preferred that said function blocks comprise functions having two inputs (X and Y) and one output (OP), said output having a limited range of values, and wherein each of said function blocks is configured to have one of the following characteristics:

(1) said output is a relatively large number if the absolute difference between X and Y is greater than a pre-set value;

(2) said output is a number less than the value of the output in (1), but preferably greater than the mid-point of the range, if the absolute difference between X and Y is greater than a second pre-set value;

(3) said output is a relatively small number if the absolute difference between X and Y is less than a third pre-set value;

(4) said output is a number greater than the value of the output in (3), but less than the output of (2) if the absolute difference between X and Y is less than a fourth pre-set value, said fourth pre-set value being larger than the third pre-set value, and less than the second pre-set value;

(5) said output is the average of X and Y.

The values X and Y will typically be calculated acceleration or velocity data.

Advantageously, the first to fourth pre-set values and the centre of the range of values, i.e. approximately equidistant from a neighbouring value and ideally are integers for ease of handling.

Also in any aspect of the invention, it is preferred that said fitness function comprises the area under the receiver operating characteristics curve.

The invention also provides apparatus for detecting bradykinesia in a subject comprising:
 a first three-dimensional position sensor adapted to be securable to a thumb of a subject;
 a second three-dimensional position sensor adapted to be securable to an opposing finger of a subject;
 a signal processor configured to process a time series of position data from said sensors using an algorithm generated by a method described herein.

The invention also provides apparatus for detecting tremor in a subject comprising:
 a three-dimensional position sensor adapted to be securable to a finger of a subject;
 a signal processor configured to process a time series of position data from said sensor using an algorithm generated by a method described herein.

The invention also provides apparatus for detecting tremor, bradykinesia or symptoms of other neurological dysfunction comprising:
 a first three-dimensional position sensor adapted to be securable to a finger of a subject;
 a second three-dimensional position sensor adapted to be securable to an opposing finger of a subject;
 a third three-dimensional position sensor adapted to be securable to a wrist of a subject;
 a signal processor configured to process a time series of position data from said sensors using an algorithm generated by a method described herein.

Preferably, said three-dimensional position, sensors are attached to a glove, often referred to as a dataglove, which can be worn by a user. Data gloves are known in the art of human-computer interaction, and have been used in the field of virtual reality simulation. Amongst other benefits, data gloves provide a convenient and quick way to attach position sensors to the fingers and/or thumbs of a user in a repeatable fashion—this is particularly important in the clinical setting where such apparatus may be used, and particularly if the subject being assessed is exhibiting signs of dementia.

More preferably, said data glove comprises multiple such sensors, thereby enabling tracking movement of fingers and thumbs.

In particularly preferred embodiments, such apparatus further comprises a three-dimensional position sensor adapted to be securable to the wrist of a subject. In this way, a data glove providing data only on the relative three-dimensional position of fingers and thumbs may be used, with the three-dimensional wrist position sensor being used to measure absolute position of the user's hand.

BRIEF DESCRIPTION OF THE DRAWINGS

The invention will be described with reference to the accompanying drawings in which.

DESCRIPTION OF PREFERRED EMBODIMENTS

Methods and apparatus for detecting neurological dysfunctions are described herein, and rely on data sets obtained from patients having neurological dysfunction as well as control subjects for evolution of algorithms. A number of tasks may be performed by the subjects to obtain the necessary data, corresponding to tasks that may subsequently be used in order to put the methods and apparatus into use.

Tapping Task:

In this task, a subject is asked to tap their thumb and a finger of the same hand together repeatedly. Typically, a subject would be asked to perform such a tapping movement as fast as they can over a period of 30 seconds. The task would preferably be repeated for each hand.

Prehension Task:

This task is essentially concerned with a subject being required to reach for an object with their hand, and to grasp and lift the object. The subject then returns the object to its original position. In a typical test, the subject will be seated at a table, and an object, such as a cylinder or beaker is placed on the table before them, within easy arm's reach. The subject is asked to reach out and grasp the cylinder, and lift it from the table. The object is then returned to the table by the subject. In particular embodiments of the test, an 8 cm diameter cylinder would be used, placed 27 cm in front of a subject. This type of task is also known as a "reach and grasp" task. This task typically involves four tasks to be carried out by each hand. The particular tasks are:
1. a self-guided task initiated by audio cue;
2. a visually cued task. For example, the cylinder lights up on instruction from the computer;
3. a second self-guided task initiated by audio cue. This detects any effect carried over from the previous visually cued task 2;
4. a memory-guided task initiated by an audio cue in which the subject closes their eyes and then receives an audio cue 2-5 seconds later to initiate the task. The eyes are kept closed whilst the subject reaches for the cylinder.

The subject may preferably be asked to carry out the task consecutively with each hand.

Figure 1:
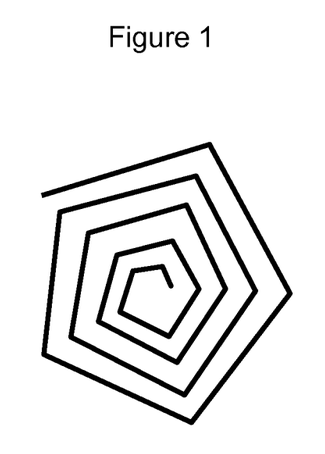
FIG. 1 illustrates a polygonal spiral.
Figure 2:
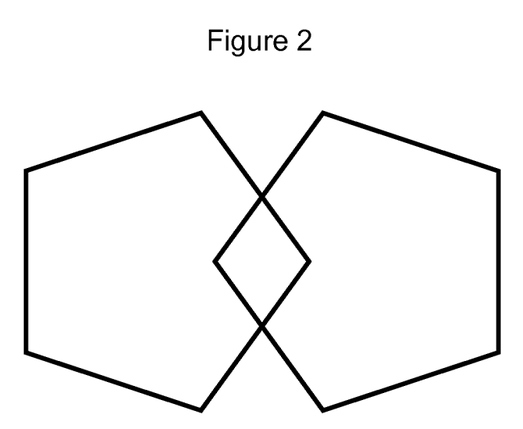
FIG. 2 illustrates interlinked pentagons.
Figure 3:
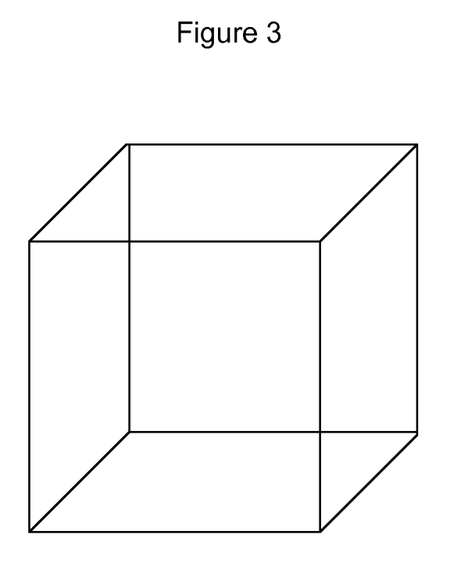
FIG. 3 illustrates a wire cube.

Constructional Task:

This task is concerned with concerned with copying a geometric figure. A subject may be asked to copy a figure provided, or to trace over such a figure with a pen. Particularly useful figures for such a task involve those needing a distinct change of direction of a pen, and a typical example is a pentagonal spiral such as that illustrated in FIG. 1, interlocking pentagons as illustrated in FIG. 2, or the wire cube of FIG. 3. Again, the subject may preferably be asked to carry out the task consecutively with each hand.

Measuring Equipment

Figure 5:
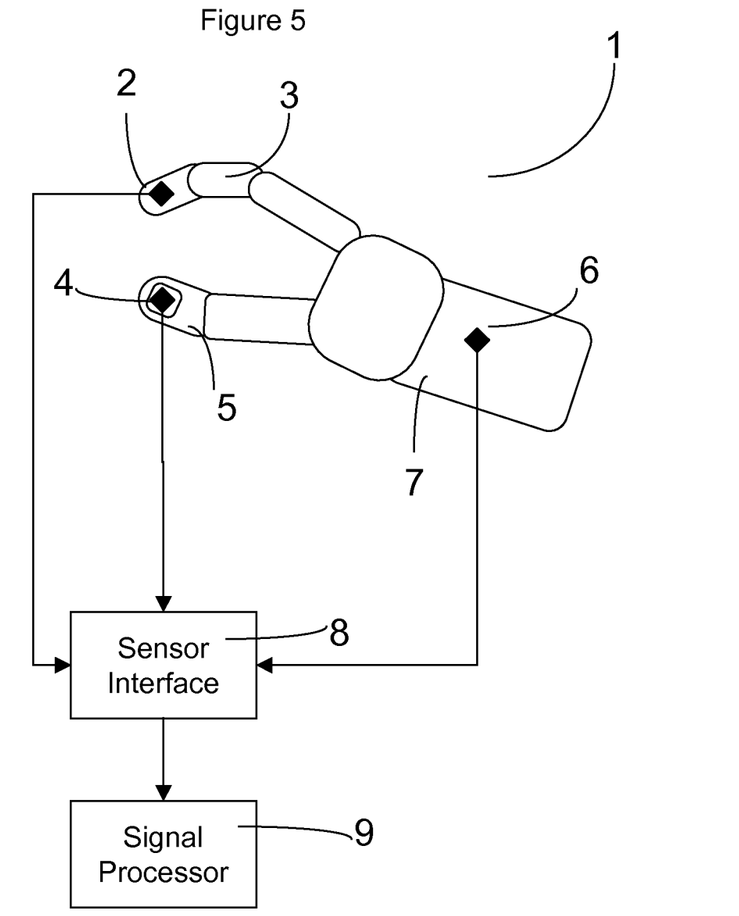
FIG. 5 illustrates apparatus according to the invention.

FIG. 5 illustrates, schematically, apparatus according to an embodiment of the invention, generally indicated by 1, comprising a first three-dimensional position sensor 2 securable to the thumb 3 of a user; a second three-dimensional position sensor 4, securable to a second opposable finger 5 of a user; and a third three-dimensional position sensor 6, securable to a wrist 7 of a user. Signals representing three-dimensional position data from the sensors are relayed via a sensor interface 8 to signal processor 9 embodying an algorithm described herein. In preferred embodiments, the wrist sensor 6 provides three-dimensional position data relative to a fixed datum point whilst the finger sensors provide position data relative to the wrist sensor 6. In this way, the position of the fingers relative to the fixed datum point may readily be calculated whilst allowing smaller and less costly sensors to be applied to the fingers. In particularly preferred embodiments said sensors may be provided incorporated in a data glove. In an alternative embodiment, sensors attached to the fingers and thumbs are used to detect and measure the distance from one or more of the other sensors. For example measurement can be made of the distance between the sensor on the thumb and the sensor on the opposable finger.

Such a preferred form of data glove may be made from stretch fabric such as Lycra® and have sensors attached at locations on the glove. This makes fitting of the sensors to a user's hand and fingers more convenient, which is especially important in the clinical context where it is most likely to be used. An example of such a "data glove" is the "Data Glove Ultra Series" available from 5DT Inc., Irvine, Calif., USA. This contains 14 sensors in total to measure complete movement of the hand. Two sensors are provided per finger, one sensor for the knuckle, one for the first joint of the hand and abduction sensors between fingers. Movements from each sensor are reported at a minimum rate of 75 Hz.

Data Processing

The distance between any two sensors comprised in the measuring equipment may readily be calculated from their respective 3-dimensional $(x_i, y_i, z_i)$ spatial coordinates by application of a standard Pythagorean equation of the form:

$$\text{Distance} = [(x_1-x_2)^2 + (y_1-y_2)^2 + (z_1-z_2)^2]^{0.5}$$

The inventor has found, surprisingly, that limiting (or "clipping") the data obtained from experimental tasks significantly improves the fitness of CGP algorithms evolved by the techniques disclosed herein. Normalisation of the data can also provide advantages.

The velocity data were limited by calculating an upper and lower limit, within which limits the data were clipped. The mean and the standard deviation for each of the velocity profiles were calculated—the upper limit for each set of velocity data was computed as the mean velocity plus the standard deviation, and the lower limit for each set of velocity data was computed as the mean velocity minus the standard deviation. Any data in the velocity profile that was above the upper limit was truncated to the value of the upper limit and any data in the velocity profile below the lower limit was truncated to the value of the lower limit.

It was found that limiting of the data in the velocity profiles, as explained above, was beneficial to the fitness of the CGP evolved. Surprisingly, a higher fitness was achieved when the velocity data was limited compared to when it was not limited.

As an example of data pre-processing for production of a signal-processing algorithm of the invention, acceleration within a patient or control data set was calculated from the difference in the velocity data between consecutive samples. After trying different ranges of gradients for the quantisation levels and different numbers of quantisation levels, it was found that 22 encoding levels would be used for the final acceleration based encoding scheme, as shown below (where 'gradient' is the acceleration as calculated over the distance between the two sensors). In this example the units are in cm/sample at 30 Hz which gives units of: ($\times 300$ mm/sec$^2$).

| Gradient range | Gradient Encoding |
| --- | --- |
| gradient >= 0.250 | 21 |
| 0.250 > gradient >= 0.225 | 20 |
| 0.225 > gradient >= 0.200 | 19 |
| 0.200 > gradient >= 0.175 | 18 |
| 0.175 > gradient >= 0.150 | 17 |
| 0.150 > gradient >= 0.125 | 16 |
| 0.125 > gradient >= 0.100 | 15 |
| 0.100 > gradient >= 0.075 | 14 |
| 0.075 > gradient >= 0.050 | 13 |
| 0.050 > gradient >= 0.025 | 12 |
| 0.025 > gradient >= 0.000 | 11 |
| 0.000 > gradient >= −0.025 | 10 |
| −0.025 > gradient >= −0.050 | 9 |
| −0.050 > gradient >= −0.075 | 8 |
| −0.075 > gradient >= −0.100 | 7 |
| −0.100 > gradient >= −0.125 | 6 |
| −0.125 > gradient >= −0.150 | 5 |
| −0.150 > gradient >= −0.175 | 4 |
| −0.175 > gradient >= −0.200 | 3 |

-continued

| Gradient range | Gradient Encoding |
|---|---|
| −0.200 > gradient >= −0.225 | 2 |
| −0.225 > gradient >= −0.250 | 1 |
| −0.250 > gradient | 0 |

This is a linear gradient encoding system, with each band of gradients having the same width.

In a typical embodiment of the invention, velocity data may be gathered for a period of approximately 30 seconds (typically between 15 and 60, 90 or even 120 seconds or more), with a sampling frequency of approximately 30 Hz (typically between 10 Hz and 100 Hz). The velocity data would be "clipped" to within one standard deviation of the mean velocity, and a moving average filter with a window size of 2 used to smooth the velocity-limited data. Then, acceleration data would be produced from adjacent velocity data points, and the resulting acceleration data encoded to quantized levels using an encoding scheme such as the one described above. Alternatively, the acceleration data can be calculated directly from the position data.

Having encoded the data as described above, a series of function blocks and the fitness function are provided for the CGP network. The CGP may then be evolved and the network parameterised in order to develop the optimum CGP network. The CGP is trained using a training set of data as described herein.

A particularly preferred form of CGP uses a conventional elitist strategy, where the number of individuals specified by the user represents the number of genes that are evolved in each generation. At the end of each generation the fitness of the genes evolved are compared and the genes with the highest fitnesses promoted to the next generation. Here it is copied until there are the correct numbers of individuals in the new generation—each of the copies is then mutated by the mutation rates specified, and then the fitness of the genes re-calculated.

Figure 4:
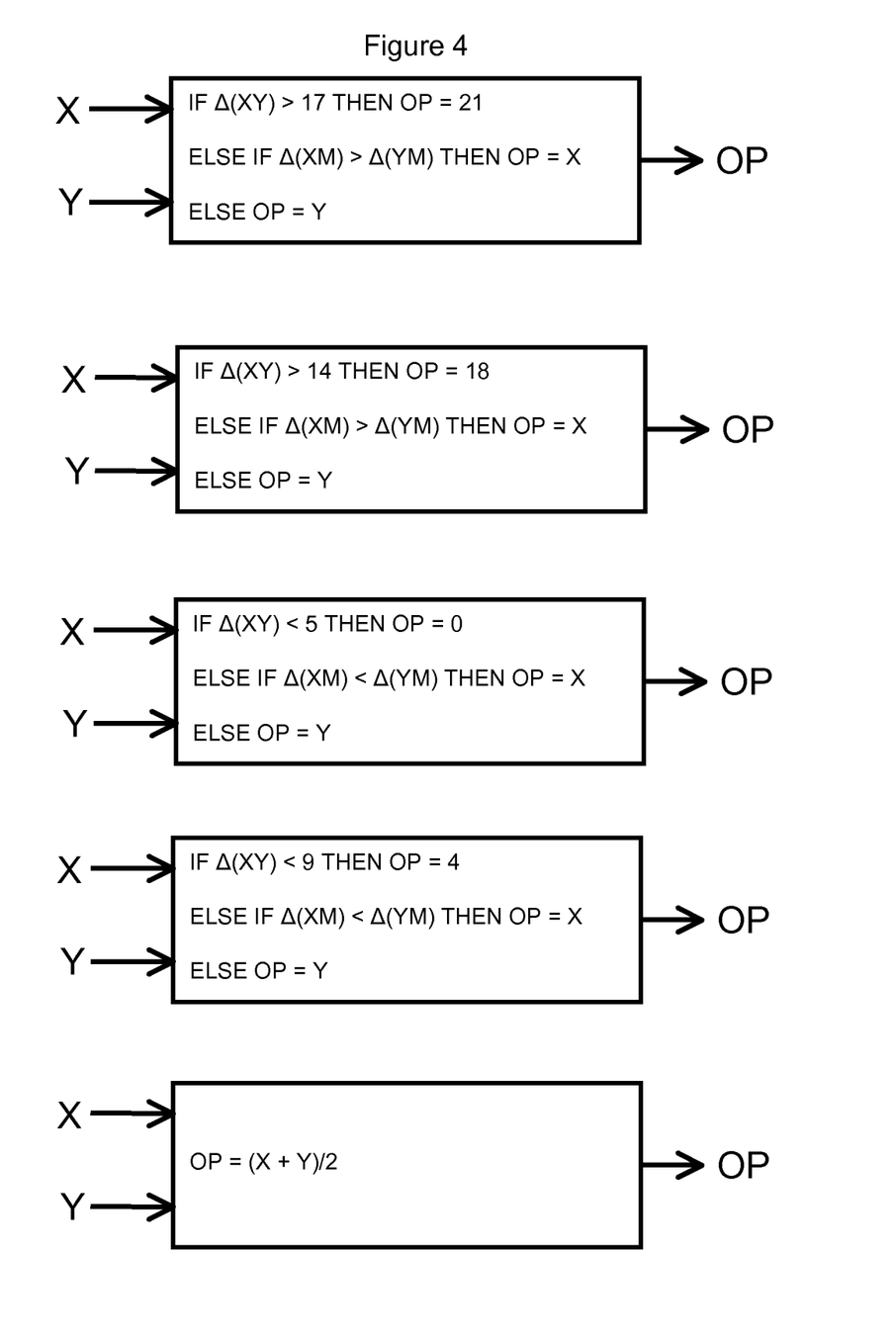
FIG. 4 illustrates a range of preferred function blocks for a CGP network.

The inventor has found that a number of function blocks of particular form provides surprisingly increased fitness of the evolved algorithms. The preferred functional blocks are described below, and illustrated in FIG. 4, with reference to the encoding scheme above in which the quantised levels are between 0 and 21, and where 'X' is the first input to the function, 'Y' is the second input to the function and 'OP' is the output of the function:

$\Delta(XY)$ is defined as the absolute difference between the inputs, i.e. ABS(X−Y);

$\Delta(XM)$ is defined as the absolute difference between the X input and the mean value of the acceleration encoding scheme, so for the encoding scheme described above:

$\Delta(XM)=ABS(X-11)$;

$\Delta(YM)$ is defined as the absolute difference between the Y input and the mean value of the acceleration encoding scheme, so for the encoding scheme described above:

$\Delta(YM)=ABS(Y-11)$.

| Function number | Function performed |
|---|---|
| 1 | IF $\Delta(XY) > 17$ THEN OP = 21<br>ELSE IF $\Delta(XM) > \Delta(YM)$ THEN OP = X<br>ELSE OP = Y |
| 2 | IF $\Delta(XY) > 14$ THEN OP = 18<br>ELSE IF $\Delta(XM) > \Delta(YM)$ THEN OP = X<br>ELSE OP = Y |
| 3 | IF $\Delta(XY) < 5$ THEN OP = 0<br>ELSE IF $\Delta(XM) < \Delta(YM)$ THEN OP = X<br>ELSE OP = Y |
| 4 | IF $\Delta(XY) < 9$ THEN OP = 4<br>ELSE IF $\Delta(XM) < \Delta(YM)$ THEN OP = X<br>ELSE OP = Y |
| 5 | OP = (X + Y)/2 |

As a generality, these operators may be defined by reference to values within the acceleration encoding scheme, as follows.

The encoding scheme encodes acceleration values between extreme values $E_{min}$ and $E_{max}$, representing respectively the minimum and maximum encoded values. A value $E_{mid}$ is calculated, being the mid-point of the encoding range, i.e. $(E_{max}-E_{min})/2$. For an integer-encoding scheme, the result may be rounded up or down to the nearest integer.

Four further values are defined: $E_{high}$ and $E_{xhigh}$, representing "high" and "extra high" values, and $E_{low}$ and $E_{xlow}$, representing "low" and "extra-low" values. Typically, the further values $E_{high}$ and $E_{xhigh}$ will be set at the value and preferably the nearest integer one-third and two-thirds of the difference between $E_{max}$ and $E_{mid}$ greater than $E_{mid}$ respectively. Similarly, $E_{low}$ and $E_{xlow}$ are one-third and two-thirds of the difference between $E_{min}$ and $E_{mid}$, lower than $E_{mid}$ respectively.

For the encoding scheme described above with 22 encoding levels, the values of these parameters are:

| Parameter | Value |
|---|---|
| $E_{max}$ | 21 |
| $E_{xhigh}$ | 18 |
| $E_{high}$ | 15 |
| $E_{mid}$ | 11 |
| $E_{low}$ | 8 |
| $E_{xlow}$ | 4 |
| $E_{min}$ | 0 |

For general parameterisation of the function blocks, the high, extra-high, low and extra-low values may alternatively be chosen as proportions of the overall range of the encoding scheme as follows:

| Parameter | Preferred Range |
|---|---|
| $E_{xhigh}$ | 70-95% |
| $E_{high}$ | 60-85% |
| $E_{low}$ | 15-40% |
| $E_{xlow}$ | 5-30% |

With the proviso that $E_{xhigh} > E_{high}$ and $E_{xlow} < E_{low}$.

Using this generalised notation, the function block definitions become:

| Function number | Function performed |
|---|---|
| 1 | IF $\Delta(XY) \geq E_{xhigh}$ THEN OP = $E_{max}$<br>ELSE IF $\Delta(XM) > \Delta(YM)$ THEN OP = X<br>ELSE OP = Y |
| 2 | IF $\Delta(XY) \geq E_{high}$ THEN OP = $E_{xhigh}$<br>ELSE IF $\Delta(XM) > \Delta(YM)$ THEN OP = X<br>ELSE OP = Y |

-continued

| Function number | Function performed |
| --- | --- |
| 3 | IF $\Delta(XY) \leq E_{xlow}$ THEN OP = $E_{min}$<br>ELSE IF $\Delta(XM) < \Delta(YM)$ THEN OP = X<br>ELSE OP = Y |
| 4 | IF $\Delta(XY) \leq E_{low}$ THEN OP = $E_{xlow}$<br>ELSE IF $\Delta(XM) < \Delta(YM)$ THEN OP = X<br>ELSE OP = Y |
| 5 | OP = (X + Y)/2 |

These function blocks are designed to detect the two-stage artefacts, characteristic of the neurological dysfunctions to be detected. The artefacts are the small fluctuations found in the velocity profiles of the PD patients. Where such an acceleration-based encoding scheme is used, these appear as small fluctuations in the acceleration profile around zero acceleration.

From graphs of the encoded data it could be seen that in the control subjects the encodings were generally spread across the entire range of encoding values i.e. the encoded data range was 0-21 for a large proportion of the control subjects. In the graphs of the encoded data for the control subjects, the encoded data contained large peaks, where the encodings swapped from a large deceleration (i.e. an encoding of 0) to a large acceleration (i.e. an encoding of 21) within a very short period of time. However, for the PD patients the encoded data was mostly within the central encoding values (between 7-14), which represents smaller acceleration/deceleration. The encoded data for the PD patients generally contained small peaks where the encoded values swapped from a small acceleration to a small deceleration. Therefore, the function set in the CGP was designed to detect the number of small peaks and the number of large peaks in the acceleration encoding. If the CGP detected mainly small differences in the encoded data it was more likely that the data was from a PD patient and if mostly large differences in the encoded data were found, then it was more likely that the data was from a control subject. The function blocks used within a CGP are very important—if the functional blocks in this study were not designed correctly, the CGP would not be able to distinguish the patient data from the control data.

Initially the use of seven function blocks had been attempted—three to detect large differences in the acceleration encoding, three to detect small differences in the acceleration encoding and one to perform an averaging of the inputs. However, it was found that the use of only five function blocks surprisingly gave a greater fitness. As well as producing a better network, this also meant that there are fewer variables to change, making it simpler to optimise the network. Two of the function blocks are designed to detect a large differences in the acceleration encoding, two are designed to detect a small differences in the acceleration encoding and one performs an averaging of the two inputs.

The function blocks detecting larges differences in the encoded data are designed to identify the large peaks mostly found in the control subjects, and the function blocks detecting small differences in the encoded data are designed to identify the smaller fluctuations mostly found in the PD patients.

In addition to the function blocks defined above, the following simplified function set can be used in separate evolutionary runs and the evolved network with the best fitness selected:
(1) the output is the sum of X and Y
(2) the output is the difference of X and Y
(3) the output is the mean of X and Y
(4) the output is the minimum of X and Y
(5) the output is the maximum of X and Y
(6) the output is the absolute value of X
(7) the output is the negative of X.

As an example of evolving the CGP network, a 9 row and 8 column CGP network was defined having 35 inputs. The network was randomly initiated with function blocks selected from the group defined above. A function mutation rate of 6% was used and the network evolved for 3000 generations. A fitness function was defined such that the function was incremented if the network output was less than 11 ($E_{mid}$) for patient-derived data, and incremented if the network output was more than 15 ($E_{high}$) for control-derived data.

The fitness function in this CGP is based on the desire to identify artefacts in the PD patient responses but not in the control subject's responses. The fitness function should represent how well the evolved network correlates with the algorithm's goal. The fitness function allows the comparison of chromosomes, therefore permitting the conventional elitist strategy used, to select the best chromosome from a population and it also allows the user to easily compare different networks.

In alternatively preferred embodiments, a fitness function may be defined as the area under the Receiver Operating Characteristics (ROC) curve. The use of ROC curves is described in e.g. Fawcett, "An Introduction to ROC Analysis", Pattern Recognition Letters, 27 (2006), 861-874.

The invention claimed is:

1. A method of generating a signal processing algorithm for processing signals representing finger and thumb positions for identifying subjects exhibiting bradykinesia or tremor at a required discrimination confidence, said method comprising the steps of:
   (1) receiving a plurality of patient position data sets representing tapping tests performed by a plurality of patients, wherein: each patient position data set includes a time series of data points representing three-dimensional position data of finger and thumb gathered by a sensor during tapping tests performed by a patient of the plurality of patients; the plurality of patients includes a plurality of subjects exhibiting bradykinesia or tremor;
   (2) receiving a plurality of control position data sets representing tapping tests performed by a plurality of control subjects, wherein each control position data set includes a time series of data points representing three-dimensional position data of finger and thumb gathered by the sensor during tapping tests performed by a subject of the plurality of control subjects;
   (3) processing each of the plurality of patient position data sets and each of the control position data sets to produce patient acceleration data sets and control acceleration data sets, respectively, wherein each of the patient acceleration data sets and each of the control acceleration data sets includes a time series of data points representing acceleration of the finger relative to the thumb for a corresponding tapping test;
   (4) using a processor to configure an initial Cartesian Genetic Programming (CGP) network comprising a set of function blocks and a fitness function giving a measure of the success of the CGP network in discriminating between the control acceleration data set and the patient acceleration data set, wherein the CGP network accepts a plurality of input data comprising adjacent values in an acceleration data set and produces a single output value putatively indicative of the presence or absence of bradykinesia or tremor;

(5) evolving with the processor said initial CGP network by sequential evolutionary mutation and selection towards increased fitness until said required discrimination confidence is achieved.

2. A method according to claim 1 wherein the processing of position data sets in step (3) comprises intermediate calculation of patient and control velocity data sets representing a time series of velocity data of the finger relative to the thumb for each corresponding tapping test, said velocity data sets being smoothed using a moving average filter of window size 2.

3. A method according to claim 1 wherein the processing of position data sets in step (3) comprises intermediate calculation of patient and control velocity data sets representing a time series of velocity data of the finger relative to the thumb for each corresponding tapping test, said velocity data sets being clipped to within one standard deviation of the mean velocity.

4. A method of generating a signal processing algorithm for processing signals representing finger and thumb positions for identifying subjects exhibiting bradykinesia, tremor, or other symptoms of neurological dysfunction at a required discrimination confidence, said method comprising the steps of:

(1) providing a plurality of patient position data sets, each set representing a time series of three-dimensional position data of a subject's fingers during motor function tests from each of a plurality of subjects exhibiting bradykinesia, tremor, or symptoms of other neurological dysfunction;

(2) providing a plurality of control position data sets, each set representing time series of three-dimensional position data of a subject's fingers during motor function tests from each of a plurality of control subjects;

(3) processing said position data sets to produce patient acceleration data sets and control acceleration data sets representing time series of acceleration of the fingers for each corresponding motor function test;

(4) providing a set of function blocks for construction of a Cartesian Genetic Programming (CGP) network;

(5) providing a fitness function giving a measure of the success of said CGP network in discriminating between said control acceleration data set and said patient acceleration data set;

(6) configuring an initial CGP network using said function blocks, said network accepting a plurality of input data comprising adjacent values in an acceleration data set and producing a single output value putatively indicative of the presence or absence of bradykinesia, tremor, or other neurological dysfunction;

(7) evolving said initial CGP network by sequential evolutionary mutation and selection towards increased fitness until said desired discrimination confidence is achieved.

5. A method according to claim 4 wherein said motor function test comprises a constructional task such as the tracing of a geometric figure.

6. A method according to claim 4 wherein said motor function test comprises a prehension task such as a "reach and grasp" task.

7. A method according to claim 1, any preceding claim wherein said function blocks comprise functions having two inputs (X and Y) and one output (OP), said output having a limited range of values, and wherein each of said function blocks is configured to have one of the following characteristics:

(1) said output is a relatively large number if the absolute difference between X and Y is greater than a pre-set value;

(2) said output is a number less than the value of the output in (1), but preferably greater than the mid-point of the range, if the absolute difference between X and Y is greater than a second pre-set value;

(3) said output is a relatively small number if the absolute difference between X and Y is less than a third pre-set value;

(4) said output is a number greater than the value of the output in (3), but less than the output of (2) if the absolute difference between X and Y is less than a fourth pre-set value, said fourth pre-set value being larger than the third pre-set value, and less than the second pre-set value;

(5) said output is the average of X and Y.

8. A method according to claim 7 wherein the first to fourth pre-set values and the centre of the range of values i.e. approximately equidistant from a neighbouring value and ideally are integers for ease of handling.

9. A method according to claim 1 any previous claim wherein said fitness function comprises the area under the receiver operating characteristics curve.

10. An apparatus for detecting bradykinesia in a patient using, the apparatus comprising:

a first three-dimensional position sensor adapted to be securable to a thumb of the patient and configured to gather a time series of data points representing three-dimensional position data of the thumb during tapping tests performed by the patient;

a second three-dimensional position sensor adapted to be securable to an opposing finger of the patient and configured to gather a time series of data points representing three-dimensional position data of the finger during the tapping tests performed by the patient;

a signal processor configured to:
  receive from the first three-dimensional position sensor and the second three-dimensional position sensor the time series of data points; and
  process the received time series of position data using a signal processing algorithm generated by a method comprising the steps of:
  (1) receiving a plurality of patient position data sets representing tapping tests performed by a plurality of patients, wherein:
    each patient position data set includes the time series of data points representing three-dimensional position data of finger and thumb gathered by the first three-dimensional position sensor and the second three-dimensional position sensor during tapping tests performed by a particular patient of the plurality of patients
    the plurality of patients includes a plurality of subjects exhibiting bradykinesia or tremor;
  (2) receiving a plurality of control position data sets representing tapping tests performed by a plurality of control subjects, wherein each control position data set includes the time series of data points representing three-dimensional position data of finger and thumb gathered by the first three-dimensional position sensor and the second three-dimensional position sensor during tapping tests performed by a subject of the plurality of control subjects;

(3) processing each of the plurality of patient position data sets and each of the control position data sets to produce patient acceleration data sets and control acceleration data sets, respectively, wherein each of the patient acceleration data sets and each of the control acceleration data sets includes a time series of data points representing acceleration of the finger relative to the thumb for a corresponding tapping test.

11. Apparatus for detecting bradykinesia, tremor, or other neurological dysfunction in a patient using the signal processing algorithm generated by the method of claim 4, the apparatus comprising:

a three-dimensional position sensor adapted to be securable to the finger of the patient and configured to gather the time series of data points representing three-dimensional position data of the finger during the motor function tests performed by the patient;

a signal processor configured to:
receive from the three-dimensional position sensor the time series of data points; and
process the received time series of position data using the generated signal processing algorithm.

12. The apparatus according to claim 11, wherein said three-dimensional position sensor is incorporated in a data glove.

13. The apparatus according to claim 12, wherein said data globe comprises multiple three-dimensional position sensors configured to gather the time series of data points representing three-dimensional position data of fingers and thumbs during the motor function tests performed by the patient.

14. The apparatus according to claim 13, further comprising an additional three-dimensional position sensor configured to be securable to a wrist of the patient.

* * * * *